United States Patent
Rezach (10) Patent No.: US 11,376,046 B1
(45) Date of Patent: Jul. 5, 2022

(54) SPINAL IMPLANT SYSTEM AND METHOD

(71) Applicant: Warsaw Orthopedic, Inc., Warsaw, IN (US)

(72) Inventor: William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/164,023

(22) Filed: Feb. 1, 2021

(51) Int. Cl.
*A61B 17/70* (2006.01)
*A61B 17/00* (2006.01)

(52) U.S. Cl.
CPC ...... *A61B 17/7035* (2013.01); *A61B 17/7002* (2013.01); *A61B 2017/0088* (2013.01); *A61B 2017/00477* (2013.01); *A61B 2017/00867* (2013.01); *A61B 2017/00933* (2013.01)

(58) Field of Classification Search
CPC ........... A61B 2017/00477; A61B 2017/00867; A61B 2017/0088; A61B 2017/00933; A61B 17/7035; A61B 17/7002
USPC ....... 606/264–270, 272, 276, 277, 278, 305, 606/308, 328
See application file for complete search history.

(56) References Cited

U.S. PATENT DOCUMENTS

| | | |
|---|---|---|
| 5,002,542 A | 3/1991 | Frigg |
| 5,053,034 A | 10/1991 | Olerud |
| 5,474,551 A | 12/1995 | Finn et al. |
| 5,645,544 A | 7/1997 | Tai et al. |
| 5,885,286 A | 3/1999 | Sherman et al. |
| 6,146,383 A * | 11/2000 | Studer ................ A61B 17/7035 606/256 |
| 6,183,473 B1 | 2/2001 | Ashman |
| 6,231,575 B1 | 5/2001 | Krag |
| 6,280,442 B1 * | 8/2001 | Barker ............... A61B 17/7037 606/256 |
| 6,520,962 B1 | 2/2003 | Taylor et al. |
| 6,551,318 B1 | 4/2003 | Stahurski |
| 6,565,566 B1 | 5/2003 | Wagner et al. |
| 6,602,253 B2 | 8/2003 | Richelsoph et al. |
| 6,875,211 B2 | 4/2005 | Nichols et al. |
| 7,621,941 B2 | 11/2009 | Schläpfer et al. |
| 7,674,293 B2 | 3/2010 | Kuiper et al. |
| 7,799,059 B2 | 9/2010 | Kramer et al. |
| 7,806,912 B2 | 10/2010 | Lawton et al. |
| 8,021,399 B2 | 9/2011 | Ritland |
| 8,167,908 B2 | 5/2012 | Ely et al. |

(Continued)

FOREIGN PATENT DOCUMENTS

WO 2005037067 A2 4/2005

*Primary Examiner* — Eduardo C Robert
*Assistant Examiner* — David C Comstock
(74) *Attorney, Agent, or Firm* — Sorell, Lenna & Schmidt, LLP (57) ABSTRACT

A bone fastener comprises a first member defining a plurality of grooves. A coupling member is disposed with the first member. A first band and a second band are disposable within the grooves. A second member is configured to penetrate tissue and includes a head engageable with the first band to provisionally connect the first member to the second member. The coupling member is engageable with a part to move the part relative to the first member into engagement with the second band to dispose the second band adjacent the first band to connect the first member to the second member. Systems, surgical instruments, implants and methods are disclosed.

20 Claims, 10 Drawing Sheets

(56) References Cited

U.S. PATENT DOCUMENTS

| | | | |
|---|---|---|---|
| 8,167,910 B2 | 5/2012 | Nilsson et al. | |
| 8,197,518 B2 | 6/2012 | Hammill et al. | |
| 8,246,657 B1 | 8/2012 | Samuel | |
| 8,262,700 B2 * | 9/2012 | Cho | A61B 17/7049 606/250 |
| 8,298,265 B2 | 10/2012 | Purcell et al. | |
| 8,298,275 B2 | 10/2012 | Rezach | |
| 8,304,089 B1 | 11/2012 | Song et al. | |
| 8,337,532 B1 | 12/2012 | McLean et al. | |
| 8,758,411 B1 | 6/2014 | Rayon et al. | |
| 8,882,803 B2 | 11/2014 | Iott et al. | |
| 8,998,956 B2 | 4/2015 | George et al. | |
| 8,998,957 B2 | 4/2015 | Kalfas et al. | |
| 9,101,405 B2 | 8/2015 | Dickinson et al. | |
| 9,451,994 B1 | 9/2016 | Whipple et al. | |
| 9,510,862 B2 | 12/2016 | Montello et al. | |
| 2004/0039383 A1 * | 2/2004 | Jackson | A61B 17/7091 606/270 |
| 2004/0210216 A1 | 10/2004 | Farris et al. | |
| 2004/0267264 A1 * | 12/2004 | Konieczynski | A61B 17/7037 606/289 |
| 2005/0080420 A1 * | 4/2005 | Farris | A61B 17/7038 606/261 |
| 2006/0149234 A1 * | 7/2006 | de Coninck | A61B 17/7035 606/278 |
| 2007/0100339 A1 * | 5/2007 | Clement | A61B 17/7041 606/277 |
| 2007/0238335 A1 | 10/2007 | Veldman et al. | |
| 2007/0270839 A1 | 11/2007 | Jeon et al. | |
| 2008/0108992 A1 | 5/2008 | Barry et al. | |
| 2009/0036929 A1 | 2/2009 | Reglos et al. | |
| 2011/0087287 A1 | 4/2011 | Reeder, Jr. et al. | |
| 2011/0093021 A1 | 4/2011 | Fanger et al. | |
| 2012/0197313 A1 * | 8/2012 | Cowan | A61B 17/7037 606/305 |
| 2013/0211457 A1 * | 8/2013 | Dickinson | A61B 17/7055 606/264 |
| 2014/0257411 A1 | 9/2014 | Rezach | |
| 2015/0201972 A1 * | 7/2015 | Doubler | A61B 17/7037 606/266 |
| 2016/0089187 A1 | 3/2016 | Bootwala et al. | |
| 2017/0095271 A1 | 4/2017 | Faulhaber | |
| 2017/0112540 A1 | 4/2017 | Montello et al. | |
| 2017/0202581 A1 * | 7/2017 | Barrus | A61B 17/8685 |
| 2018/0110548 A1 | 4/2018 | May et al. | |
| 2018/0206890 A1 | 7/2018 | Rezach | |
| 2019/0183535 A1 * | 6/2019 | May | A61B 17/7038 |

\* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member defining a plurality of grooves. A coupling member is disposed with the first member. A first band is configured for disposal within the grooves. A second band is configured for disposal within the grooves. A second member is configured to penetrate tissue and includes a head engageable with the first band to provisionally connect the first member to the second member. A part is releasably engaged with the first member. The coupling member is engageable with the part to move the part relative to the first member into engagement with the second band to dispose the second band adjacent the first band to connect the first member to the second member. In some embodiments, systems, surgical instruments, implants and methods are disclosed.

In one embodiment, a single level spinal construct is provided. The single level spinal construct comprises a first bone fastener including a body defining a plurality of grooves and including a spinal rod support. A set screw is disposed with the body. A first band is configured for disposal within the grooves and a second band is configured for disposal within the grooves. A shaft is configured to penetrate tissue and includes a head engageable with the first band to provisionally connect the body to the shaft. A crown is releasably engaged with the body such that the set screw is engageable with the crown to move the crown relative to the body into engagement with the second band to dispose the second band adjacent the first band to connect the body to the shaft. The single level spinal construct comprises a second bone fastener and a spinal rod support.

In one embodiment, a spinal implant system is provided. The spinal implant system comprises at least one bone fastener including a body defining a plurality of grooves. A set screw is disposed with the body. A first band is configured for disposal within the grooves and a second band is configured for disposal within the grooves. A shaft is configured to penetrate tissue and includes a head engageable with the first band to provisionally connect the body to the shaft. A crown is releasably engaged with the body such that the set screw is engageable with the crown to move the crown relative to the body into engagement with the second band to dispose the second band adjacent the first band to connect the body to the shaft. The body is selected from a plurality of alternate bodies and the shaft includes a mating surface engageable with the body such that the shaft is interchangeable with the plurality of bodies.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct including a bone fastener. In some embodiments, the spinal construct includes a single vertebral level bone fastener that is employed with a method of surgical treatment including compression of vertebrae. In some embodiments, the spinal construct includes a low profile single vertebral level bone fastener that can be utilized with a modular screw platform. In some embodiments, the spinal construct is employed with single vertebral level degenerative procedures.

In some embodiments, the present surgical system includes a spinal construct including two bone fasteners and a spinal implant including a spinal rod. In some embodiments, the spinal construct includes at least one bone fastener having a breakoff set screw, a receiver, a rod clamp, a crown, an upper ring, a lower ring, and a bone screw shaft. In some embodiments, the bone fasteners each include a threaded set screw. In some embodiments, the threaded set screw is configured to secure an implant, including clamping a spinal rod to the bone fastener by implementing a selected amount of force. In some embodiments, the crown is pushed in a downward direction to engage the receiver in a snap fit engagement and to overcome friction generated from engagement between a circumferential flange of the crown and a projection defined from an inner surface of the receiver. In some embodiments, the set screw is secured, for example, clamped onto a head of the shaft, for example, in a locked position. In some embodiments, the set screw is secured onto the rod, for example, clamped onto the rod. In some embodiments, the set screw will break from the bone fastener at a predetermined torque. In some embodiments, the set screw overlaps with the crown for additional stability. In some embodiments, an interior surface of the receiver and an exterior surface of the crown engage in a snap fit engagement. In some embodiments, the snap fit engagement provides friction that is overcome during locking of an implant. In some embodiments, the present surgical system includes one or more bone fasteners.

In some embodiments, the present surgical system includes a spinal construct including a bone fastener that reduces surgical procedure time. In some embodiments, the bone fastener eliminates in situ placement of set screws. In some embodiments, the bone fastener provides a low profile implant. In some embodiments, the bone fastener is a pre-assembled single vertebral level bone fastener. In some embodiments, the bone fastener is compatible with modular bone fasteners.

In some embodiments, the present surgical system includes one or more spinal constructs, including bone fasteners and is employed with a method of surgical treatment including secure attachment of the one or more spinal constructs to a surgical site. In some embodiments, the method includes the step of determining a selected trajectory of bone fastener insertion. In some embodiments, the selected trajectory includes a traditional trajectory, a cortical trajectory, a medial to lateral trajectory, or an anteroposterior trajectory. In some embodiments, the method includes the step of inserting a shaft of a bone fastener into a surgical site. In some embodiments, the method includes the step of connecting components of the bone fastener with the bone fastener shaft. In some embodiments, the components of the bone fastener shaft include a lower ring, an upper ring, a crown, a receiver, a rod clamp and/or a break off set screw. In some embodiments, the method includes the step of applying a force in an upward direction on the bone fastener to confirm attachment. In some embodiments, the method includes the step of applying compression to vertebrae. In some embodiments, the method includes the step of tightening the set screw to lock the bone fastener. In some embodiments, one or more bone fasteners can be employed.

In some embodiments, the present surgical system includes a spinal construct that includes a connector employed in a revision surgery. In some embodiments, the connector is configured to attach to one or more existing spinal constructs implanted with a surgical site, for example, a body of a patient. In some embodiments, the present surgical system includes a spinal construct that can be employed in a revision surgery to connect to an existing spinal rod implanted with the body. In some embodiments, the present surgical system includes a spinal construct that can be employed in a revision surgery to connect to an existing bone fastener and/or spinal rod construct through a minimally invasive approach.

In some embodiments, the present surgical system includes a spinal construct that can be employed with a method for treating a spine. In some embodiments, the method includes the step of removing a set screw from a receiver of a bone fastener. In some embodiments, the method includes the step of sliding a spinal rod out of an implant receiver, for example, a rod clamp. In some embodiments, the method includes the step of engaging a bone fastener with a surgical instrument, for example, a driver.

In some embodiments, the present surgical system includes one or more spinal constructs that can be employed with a method of surgical treatment including secure attachment of the spinal constructs to a surgical site. In some embodiments, the method includes the step of inserting bone fastener shafts, for example, a first bone fastener shaft and a second bone fastener shaft within a surgical site. In some embodiments, the method comprises the step of connecting a spinal construct onto each of the bone fastener shafts. In some embodiments, the spinal construct includes a reduced medial-lateral width and an enlarged dorsal profile relative to a standard spinal construct. In some embodiments, the medial-lateral width is 17.5 millimeters (mm). In some embodiments, the dorsal profile is 15 mm. In some embodiments, the method includes the step of advancing a set screw to drive a crown. In some embodiments, the set screw is advanced to lock the modular connection to the bone fastener. In some embodiments, the set screw is advanced to lock the position of the spinal construct relative to the bone fastener shaft. In some embodiments, the set screw is advanced to translate an arm in an upward direction to lock the bone fastener shaft. In some embodiments, an interior surface of the spinal construct includes a swaged thread or is laser spot welded so the set screw does not unintentionally advance through the spinal construct. In some embodiments, the spinal construct includes an enlarged medial-lateral width and a reduced dorsal profile relative to a standard spinal construct. In some embodiments, the medial-lateral width is 18 millimeters (mm). In some embodiments, the dorsal profile is 14 mm.

In some embodiments, one or all of the components of the surgical system may be disposable, peel-pack, pre-packed sterile devices. In some embodiments, one or all of the components of the surgical system may be reusable. In some embodiments, the surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-19, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 1:
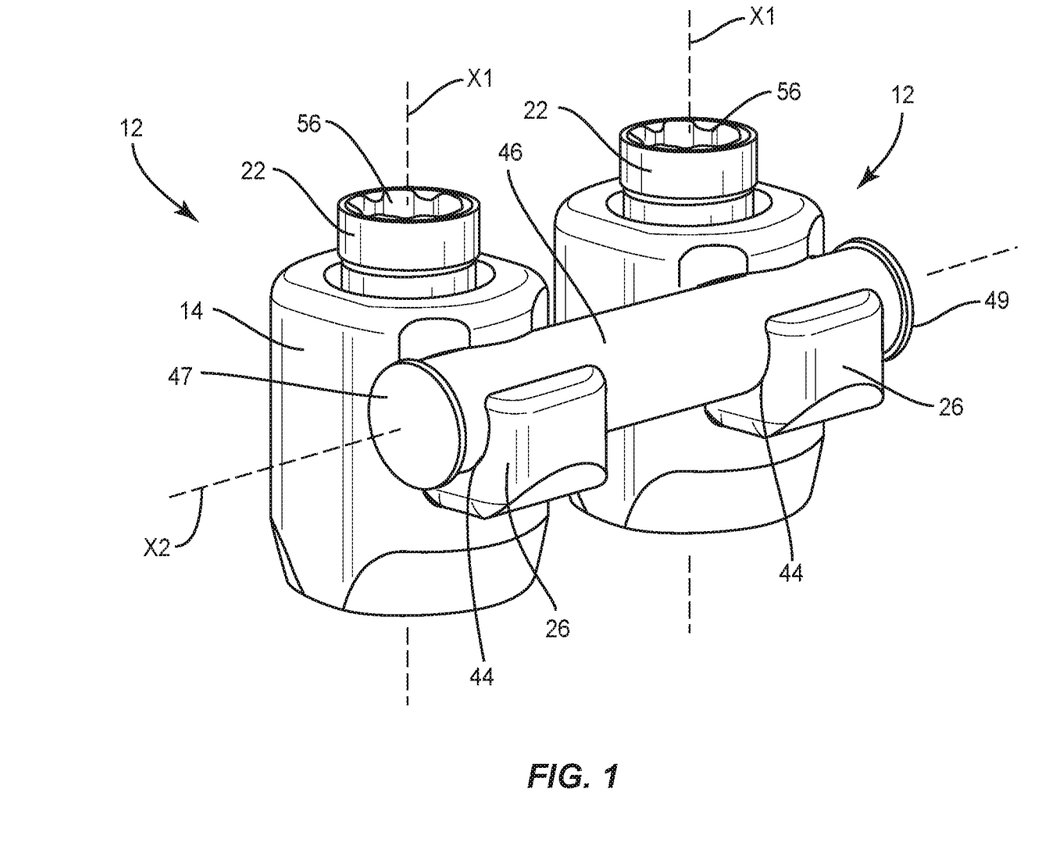
FIG. 1 is a perspective view of components of one embodiment of a system in accordance with the principles of the present disclosure.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. Spinal implant system 10 comprises one or more spinal constructs including a spinal implant, for example, one or more bone fasteners 12. In some embodiments, spinal implant system 10 is configured for use as a single vertebral level spinal construct that allows for compression of relative vertebrae, as described herein. In some embodiments, spinal implant system 10 includes a second bone fastener 12, as shown in FIG. 1.

Figure 2:
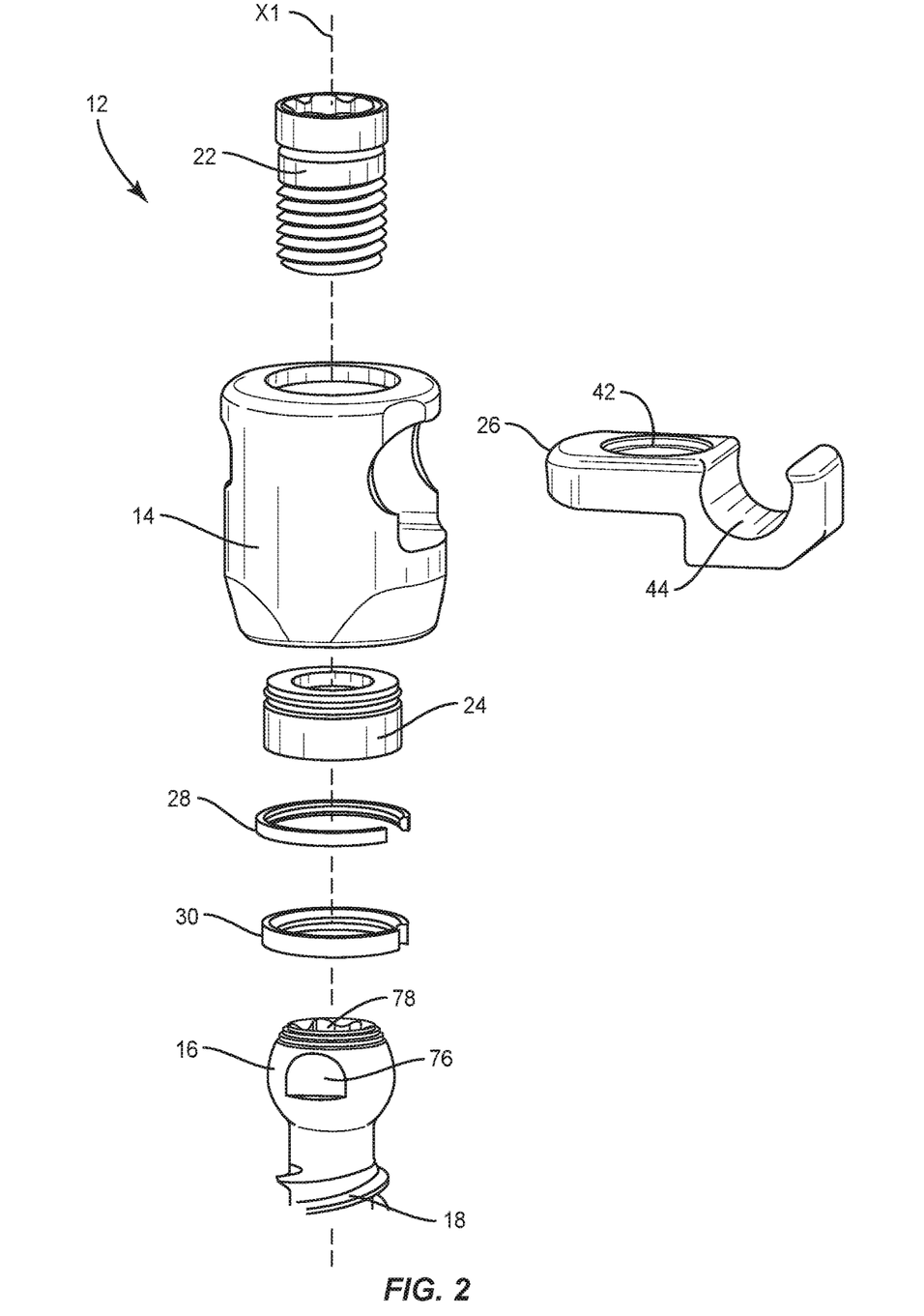
FIG. 2 is a perspective view of components of one embodiment of a system with parts separated in accordance with the principles of the present disclosure.
Figure 9:
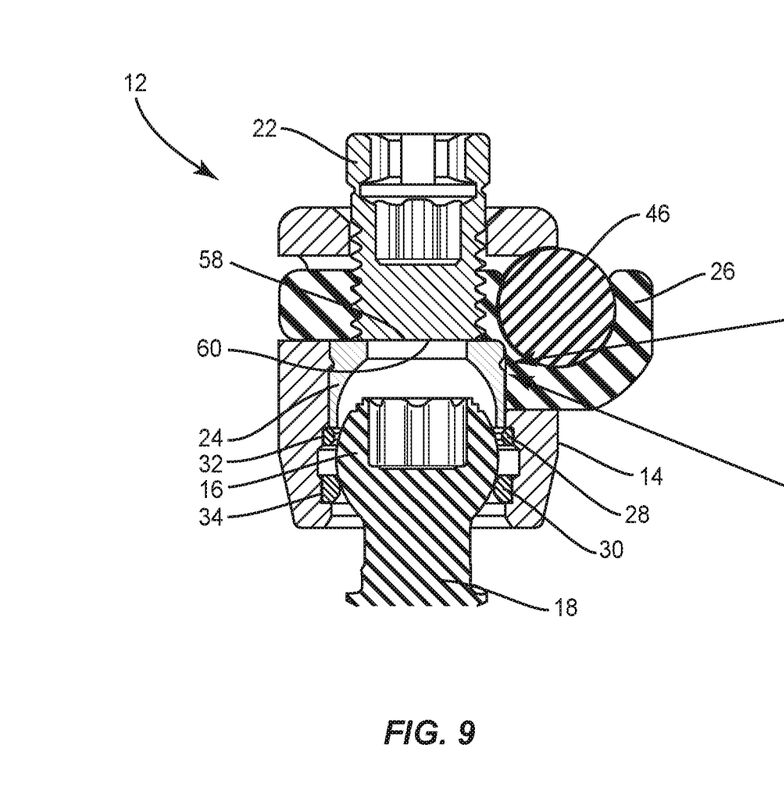
FIG. 9 is a cross section view of components of one embodiment of a system in accordance with the principles of the present disclosure.

In some embodiments, one or more of the components of spinal implant system 10 are configured to simplify a revision procedure. Bone fastener 12 includes a member, for example, a body 14, as shown in FIG. 2. In some embodiments, body 14 includes a receiver. Body 14 is configured for connection with a member, for example, a shaft 18 via a head 16 of shaft 18, as shown in FIG. 9. Body 14 defines a longitudinal axis X1. Body 14 defines an inner surface that defines a cavity 20. Cavity 20 is configured for disposal of a coupling member, for example, a portion of a set screw 22, a part, for example, a crown 24, a portion of a spinal rod support 26, a band 28, a band 30 and head 16, as described herein and shown in FIG. 9. In some embodiments, the inner surface may have alternate surface configurations to enhance disposal or engagement, such as, for example, rough, arcuate, undulating, mesh, porous, semi-porous, dimpled and/or textured. In some embodiments, cavity 20 may have various cross section configurations, such as, for example, oval, oblong, triangular, rectangular, square, polygonal, irregular, uniform, non-uniform, variable and/or tapered.

The inner surface of body 14 defines a plurality of grooves, including a groove 32 and a groove 34, as shown in FIG. 9. Band 28 is configured for movable disposal in at least groove 32 and band 30 is configured for movable disposal in at least groove 34, as described herein. To connect and/or fix connection between body 14 and shaft 18, band 28 is expandable between a provisional capture orientation and an expanded orientation, and band 30 is expandable between a contracted orientation and an interference orientation, as shown in FIGS. 11-14 and described herein. In some embodiments, grooves 32 and 34 may have alternate surface configurations to enhance disposal with bands 28 and 30, such as, for example, rough, arcuate, undulating, mesh, porous, semi-porous, dimpled and/or textured. In some embodiments, grooves 32, 34 may be disposed in an adjacent orientation, a serial orientation and/or a lateral orientation relative to each other.

Figure 18:
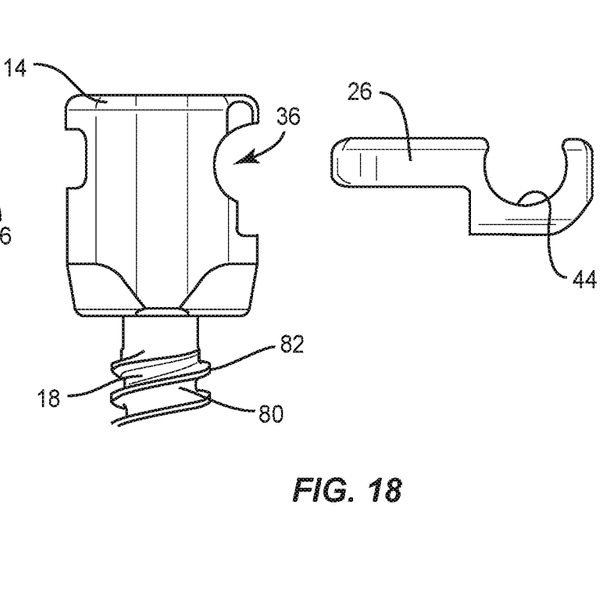
FIG. 18 is a side view of the components shown in FIG. 17.
Figure 19:
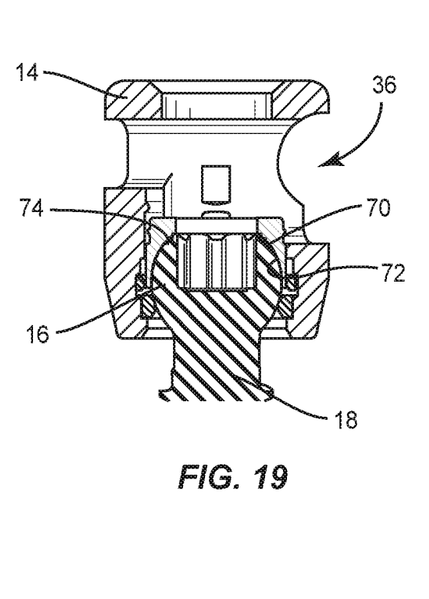
FIG. 19 is a cross section view of the components shown in FIG. 17.

An outer surface of body 14 defines a transverse opening 36, as shown in FIGS. 18 and 19. Opening 36 is configured for disposal of spinal rod support 26, as described herein. In some embodiments, opening 36 may have various cross section configurations, such as, for example, oval, oblong, triangular, rectangular, square, polygonal, irregular, uniform, non-uniform, variable and/or tapered.

Figure 5:
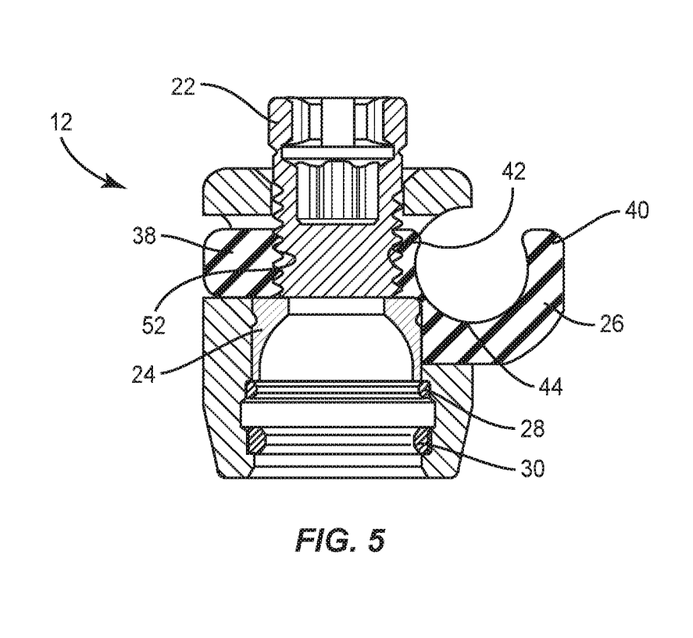
FIG. 5 is a cross section view of the components shown in FIG. 3.

Spinal rod support 26 extends between an end 38 and an end 40, as shown in FIG. 5. End 38 includes a threaded opening 42. A portion of set screw 22 is configured for disposal with opening 42, as described herein. End 40 includes a ledge 44. A spinal implant, for example, a spinal rod 46 is configured for disposal with ledge 44, as shown in FIG. 1. Ledge 44 includes an arcuate surface configured for engagement with an arcuate surface of rod 46. Rod 46 defines an axis X2. In some embodiments, ledge 44 may have alternate surface configurations to enhance disposal of rod 46, such as, for example, rough, arcuate, undulating, mesh, porous, semi-porous, dimpled and/or textured.

Figure 3:
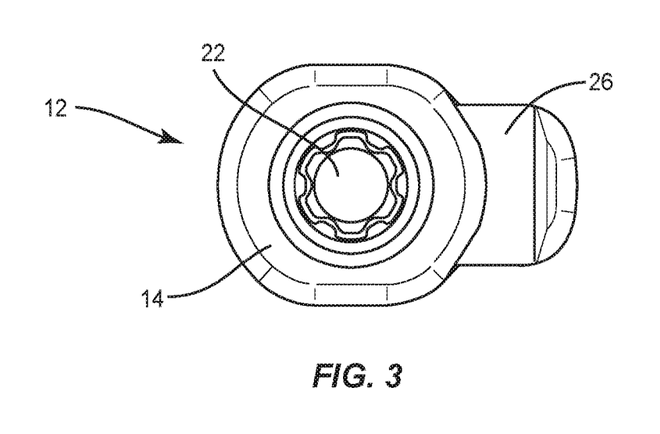
FIG. 3 is a plan view of components of one embodiment of a system in accordance with the principles of the present disclosure.
Figure 4:
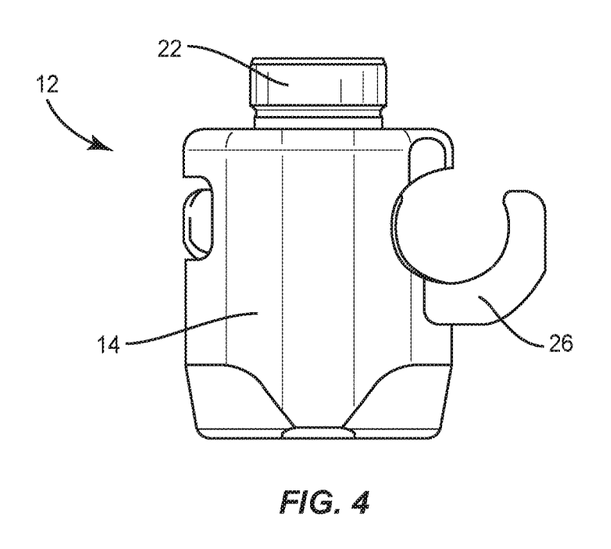
FIG. 4 is a side view of the components shown in FIG. 3.
Figure 6:
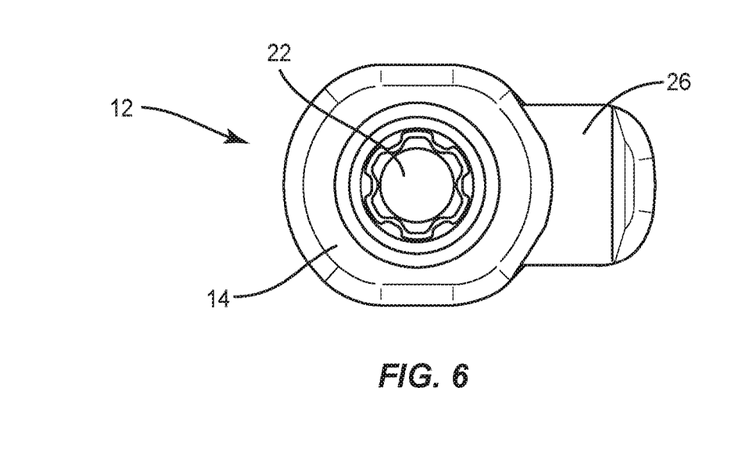
FIG. 6 is a plan view of components of one embodiment of a system in accordance with the principles of the present disclosure.
Figure 7:
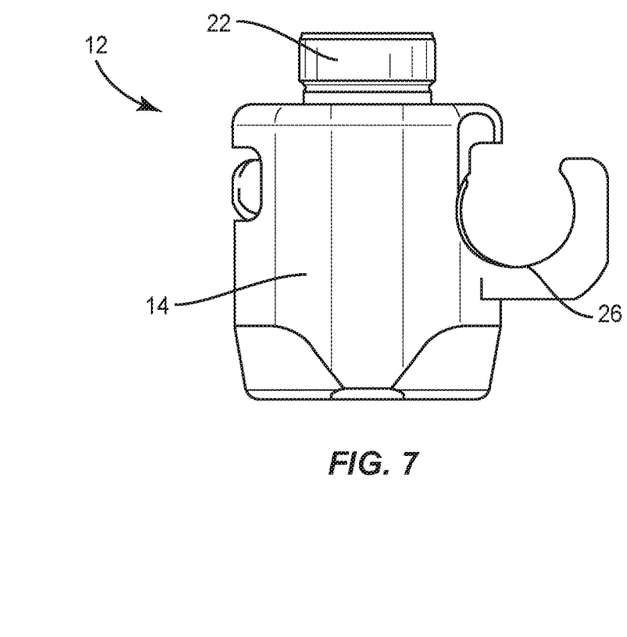
FIG. 7 is a side view of the components shown in FIG. 6.
Figure 8:
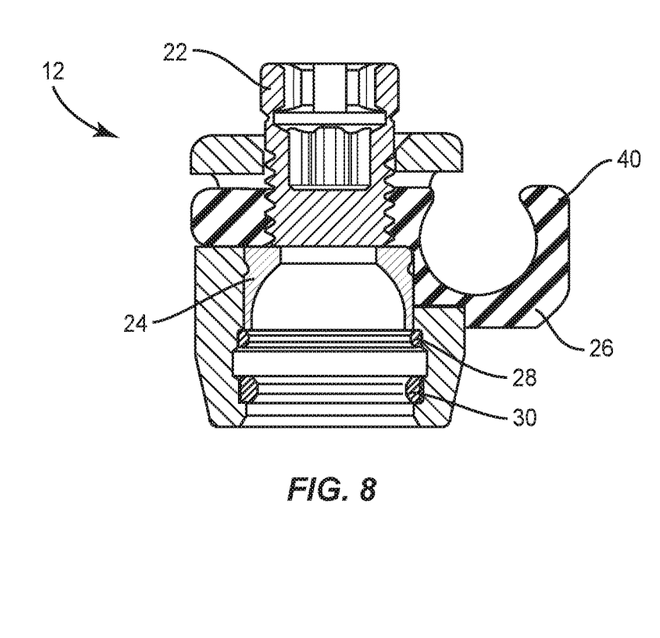
FIG. 8 is a cross section view of the components shown in FIG. 6.

In some embodiments, body 14 disposed with spinal rod support 26 includes a reduced medial-lateral width and an enlarged dorsal profile relative to a standard spinal construct, as shown in FIGS. 3-5. In some embodiments, the medial-lateral width is 17.5 millimeters (mm). In some embodiments, the dorsal profile is 15 mm. In some embodiments, body 14 disposed with spinal rod support 26 includes an enlarged medial-lateral width and a reduced dorsal profile relative to a standard spinal construct, as shown in FIGS. 6-8. In some embodiments, the medial-lateral width is 18 millimeters (mm). In some embodiments, the dorsal profile is 14 mm.

Rod 46 extends between an end 47 and an end 49, as shown in FIG. 1. In some embodiments, rod 46 may have various cross section configurations, such as, for example, circular, oval, oblong, polygonal, irregular, uniform, non-uniform, variable, offset and/or tapered. Ends 47 and 49 are configured for connection with ledges 44 of spinal rod supports 26 of bone fasteners 12, as described herein and shown in FIG. 1.

In some embodiments, axis X2 is disposed perpendicular to axis X1. In some embodiments, all or a portion of rod 46 extends in the same plane as body 14. In some embodiments, all or a portion of rod 46 extends offset relative to body 14. In some embodiments, axis X2 may be disposed at alternate orientations relative to axis X1, for example, transverse and/or other angular orientations such as acute or obtuse, coaxial and/or may be offset or staggered.

Figure 17:
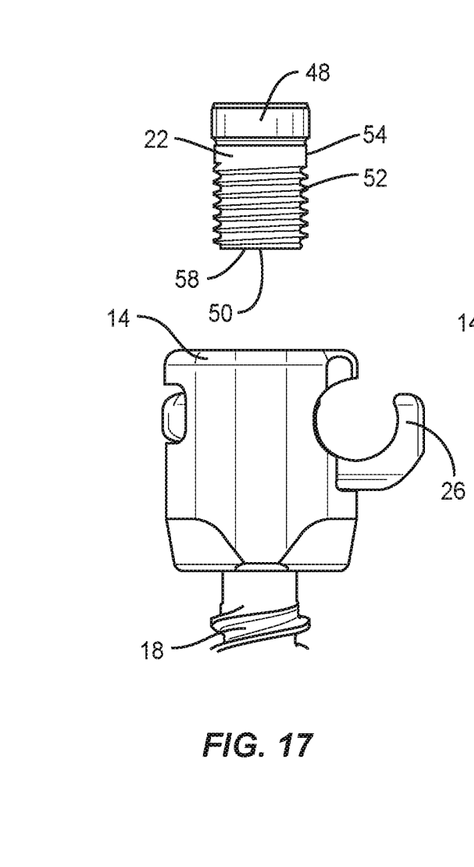
FIG. 17 is a side view of components of one embodiment of a system in accordance with the principles of the present disclosure.

Set screw 22 is configured for disposal with cavity 20 and is configured for disposal with threaded opening 42 to fix spinal rod 46 relative to body 14. Set screw 22 is configured for engagement with crown 24 to move crown 24 relative to body 12 into engagement with band 28 to dispose band 28 adjacent band 30 to connect and/or fix connection of body 12 with shaft 18, as described herein. Set screw 22 extends between an end 48 and an end 50, as shown in FIG. 17. Set screw 22 includes an outer surface, such as, for example, a thread 52, as shown in FIG. 5. Thread 52 is configured for engagement with threaded opening 42 of spinal rod support 26. In some embodiments, thread 52 includes one or a plurality of threads. In some embodiments, thread 52 is continuous along a portion of set screw 22. In some embodiments, thread 52 may include a single thread turn or a plurality of discrete threads.

End 48 includes a break off portion 54, as shown in FIG. 17. In some embodiments, break off portion 54 includes a tool engaging portion 56, as shown in FIG. 1 configured to engage a surgical tool or instrument (not shown). In some embodiments, break off portion 54 is frangibly connected to end 48. In some embodiments, break off portion 54 is fabricated from a fracturing and/or frangible material such that manipulation of break off portion 54 can fracture and separate at a predetermined force and/or torque limit. In some embodiments, as force and/or torque is applied to break off portion 54 and resistance increases, for example, due to engagement of thread 52 and threaded opening 42, as described herein, the predetermined torque and force limit is approached.

In some embodiments, break off portion 54 may be fabricated from a homogenous material or heterogeneously fabricated from different materials, and/or alternately formed of a material having a greater degree, characteristic or attribute of plastic deformability, frangible property and/or break away quality to facilitate fracture and separation of the portion.

In some embodiments, tool engaging portion 56 may have a cruciform, phillips, square, polygonal, hexalobular or star cross sectional configuration configured for disposal of a correspondingly shaped portion of a surgical tool or instrument.

End 50 includes a distal surface 58 engageable with a proximal end surface 60 of crown 24, as shown in FIG. 9. Set screw 22 is releasably fixed in rotation relative to crown 24 and is configured to apply a force to crown 24 to overcome a friction fit between body 14 and crown 24 and to axially translate crown 24 relative to body 14, as described herein. In some embodiments, surface 58 may have alternate surface configurations, for example, rough, arcuate, undulating, mesh, porous, semi-porous, dimpled and/or textured.

Figure 10:
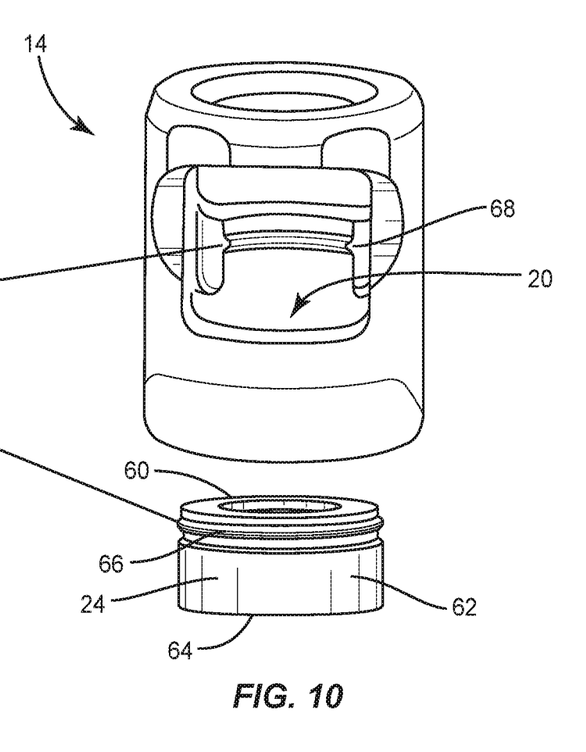
FIG. 10 is a perspective view of components of the system shown in FIG. 9.

Crown 24 is releasably engaged with body 14 and engagement of crown 24 and body 14 includes a releasable friction fit. In some embodiments, the releasable friction fit includes a snap fit and/or pop fit engagement. Crown 24 includes a circumferential wall 62 defining proximal end surface 60 and a distal end surface 64, as shown in FIG. 10. In some embodiments, all or only a portion of surfaces 60, 64 may have alternate cross section configurations, for example, oval, oblong, triangular, square, polygonal, irregular, uniform, non-uniform, offset, staggered, and/or tapered.

Wall 62 includes an outer surface that defines a projection, including a circumferential flange 66, as shown in FIG. 10. Flange 66 is configured for a releasable friction fit engagement with a projection 68 of body 14, as shown in FIGS. 9 and 10. In some embodiments, the releasable friction fit engagement provides friction that a user overcomes during locking of bone fastener 12. In some embodiments, all or only a portion of flange 66 may have alternate cross section configurations, for example, oval, oblong, triangular, square, polygonal, irregular, uniform, non-uniform, offset, staggered, and/or tapered. In some embodiments, flange 66 is disposed about all or only a portion of flange 66. In some embodiments, a user applies a force, as described herein to crown 24 in a range of 80-350 Newtons (N) to overcome the releasable friction fit between flange 66 and projection 68.

An inner surface of crown 24 defines a mating engagement portion 70 configured for engagement with a mating engagement portion 72 of head 16 of shaft 18. In some embodiments, mating engagement portion 70 includes flats 74 configured for engagement with flats 76 of mating engagement portion 72 of head 16, as shown in FIGS. 2 and 19. Flats 74 are configured to interface with flats 76 to resist and/or prevent rotation of body 14 about axis X1 in a perpendicular plane of motion. In this configuration, shaft 18 is free to rotate along a single axis and/or within a single plane relative to body 14. In some embodiments, all or only a portion of the inner surface of crown 24 may have alternate surface configurations, for example, rough, arcuate, undulating, mesh, porous, semi-porous, dimpled and/or textured.

In some embodiments, crown 24 includes an opening that is configured for disposal of a guidewire when body 14 is used in conjunction with a guidewire and is translated over the guidewire when implemented with a cannulated screw. In some embodiments, the opening is centrally located through crown 24. In some embodiments, crown 24 includes an opening that allows a revision instrument to engage a tool engaging portion 78 of head 16, as shown in FIG. 2. In some embodiments, portion 78 includes a hexagonal cross-section. In some embodiments, portion 78 may have alternative cross-sections, for example, rectangular, polygonal, hexalobe, oval, or irregular.

As described herein, body 14 is assembled with shaft 18 such that set screw 22 is translatable and applies a force to crown 24 to overcome the releasable friction fit between flange 66 of crown 24 and projection 68 of body 14 and axially translates crown 24 relative to body 14. In some embodiments, set screw 22 applies a force to crown 24 in a range of 80-350 Newtons (N) to overcome the friction fit.

In some embodiments, body 14 and shaft 18 are engageable in a snap-fit assembly. In some embodiments, body 14 and shaft 18 are engageable in a pop-on assembly. In some embodiments, body 14 and shaft 18 are engageable in various fixation configurations, for example, friction fit, pressure fit, locking keyway and/or adhesive. Shaft 18 is configured to penetrate tissue while head 16 is engageable with band 28 to provisionally connect body 14 with shaft 18, as described herein. Crown 24 is releasably engaged with body 14 such that set screw 22 is engageable with crown 24 to move crown 24 relative to body 14 into engagement with band 28 to dispose band 28 adjacent band 30 to connect and/or fix connection of body 14 and shaft 18, as described herein.

Shaft 18 includes an outer surface 80 having an external thread form 82, as shown in FIG. 18. In some embodiments, the external thread form may include a single thread turn or a plurality of discrete threads. In some embodiments, other engaging structures may be located along surface 80, in place of or in addition to thread form 82 configurations discussed above, for example, a nail configuration, barbs, expanding elements, raised elements and/or spikes to facilitate engagement with tissue, for example, vertebral tissue. Alternatively, in some embodiments, surface 80 may have various surface configurations, for example, rough, arcuate, undulating, porous, semi-porous, dimpled, polished and/or textured.

In some embodiments, spinal implant system 10 can include one or a plurality of bone fasteners 12 such as those described herein, which may be employed with a single vertebral level or a plurality of vertebral levels. In some embodiments, one or more bone fasteners 12 may be engaged with vertebrae in various orientations, such as, for example, series, parallel, offset, staggered and/or alternate vertebral levels. In some embodiments, one or more bone fasteners 12 may be employed with multi-axial screws, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, includes shaft 16 for connection with body 14, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, shaft 18 is selected from a kit of a plurality of alternate shafts 18 for interchangeable connection with body 14. In some embodiments, the kit includes a plurality of alternate bodies 14 that body 14 is selected from for interchangeable connection with selected shaft 18. In some embodiments, the kit includes a variety of shafts 18 having different movement configurations when assembled with an interchangeable body 14, for example, multi-axial movement, sagittal angulation movement, fixed axis movement, mono-axial movement and/or uni-planar movement.

Figure 11:
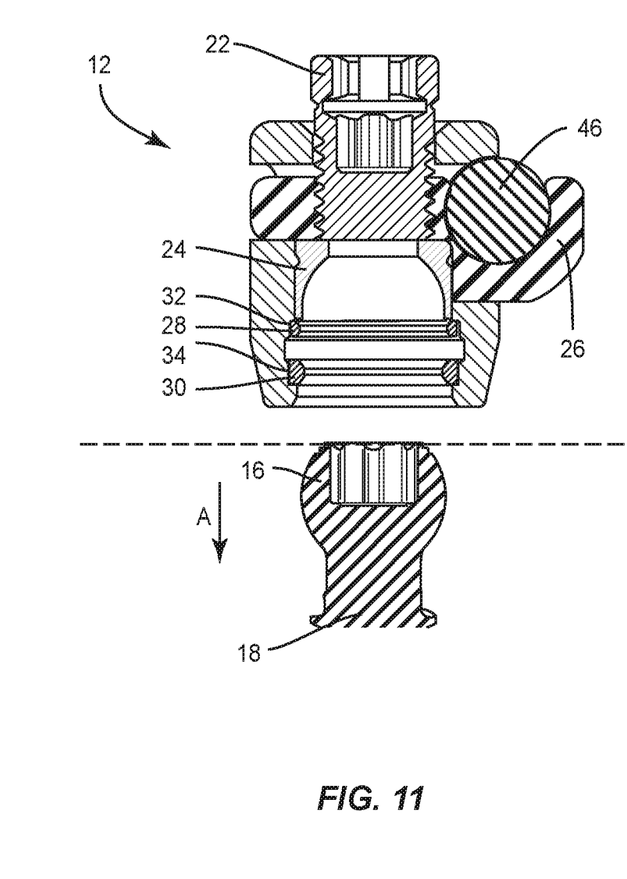
FIG. 11 is a cross section view of components of one embodiment of a system in accordance with the principles of the present disclosure.
Figure 12:
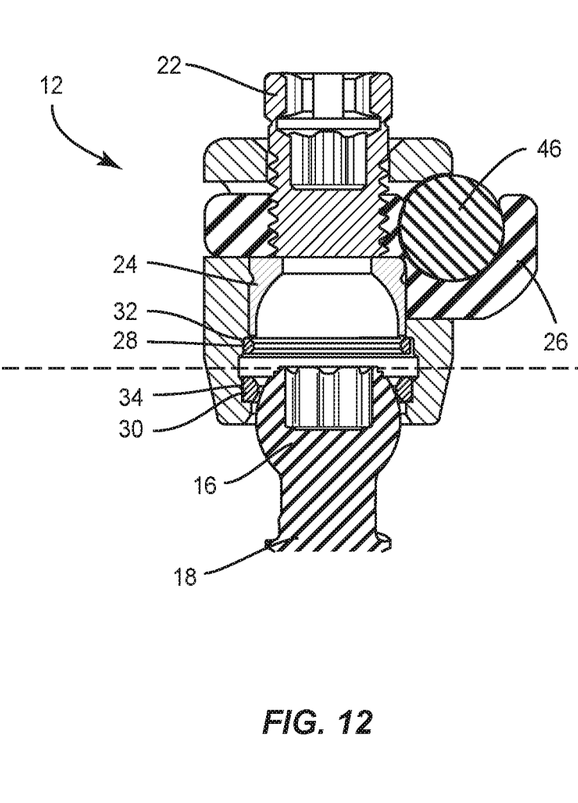
FIG. 12 is a cross section view of the components shown in FIG. 11.
Figure 13:
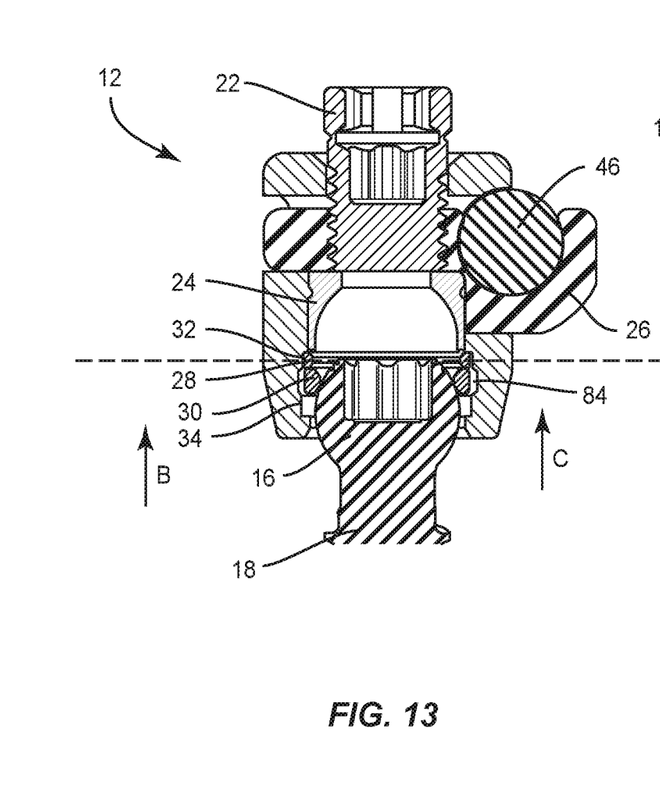
FIG. 13 is a cross section view of the components shown in FIG. 11.

In some embodiments, body 14 is assembled with set screw 22, spinal rod support 26, crown 24, band 28 and band 30, as shown in FIG. 5. Band 28 is disposed with groove 32 and band 30 is disposed with groove 34 in a contracted orientation, as shown in FIG. 11. Shaft 18 is engageable, as described herein, with body 14, as shown in FIG. 19. Body 14 is assembled with shaft 18 by translating body 14, in a direction shown by arrow A in FIG. 11. Engagement of head 16 with body 14 causes a surface of head 16 to engage band 30 such that band 30 is translated, in a direction shown by arrow B in FIG. 13, disposing band 30 into a groove 84 in an expanded orientation. Head 16 translates further through body 14 in a direction shown by arrow C in FIG. 13 and passes further through band 30 as band 30 remains in groove 84. Band 30 resiliently contracts into its natural state around head 16 as flats 76 engage with flats 74 of crown 24 to provisionally capture shaft 18, as shown in FIG. 14.

Figure 14:
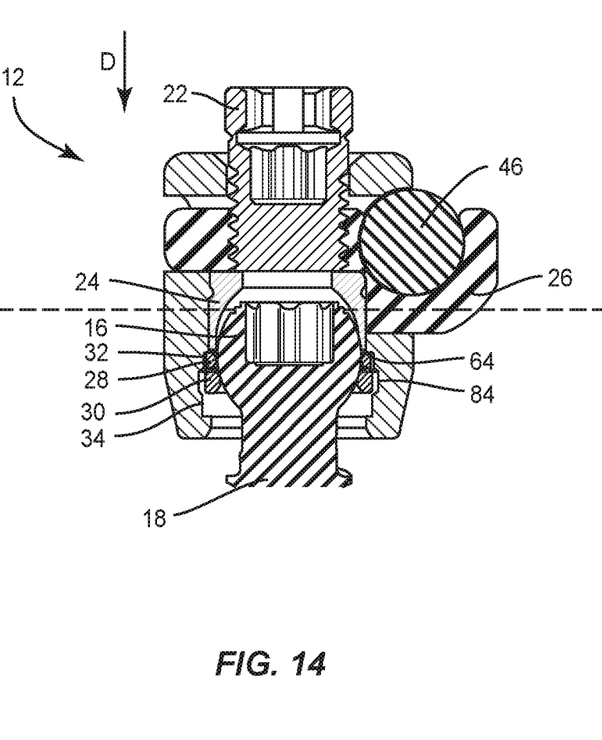
FIG. 14 is a cross section view of the components shown in FIG. 11.

Crown 24 is manipulated, for example, via engagement by set screw 22 to translate crown 24, in a direction, for example, an axial direction, shown by arrow D in FIG. 14. Set screw 22 is translatable and applies a force to crown 24 to overcome the releasable friction fit between flange 66 of crown 24 and projection 68 of body 14. Distal end surface 64 of crown 24 engages band 28 to dispose band 28 adjacent band 30 to connect and/or fix connection of body 14 and shaft 18, as shown in FIG. 14. Band 28 is oriented for abutting and/or contacting engagement with band 30 to force band 30 back into groove 34, and thus providing fixed connection of the components of bone fastener 12. A second bone fastener 12 is attached to the surgical site similar to that described herein. Spinal rod 46 is disposed with ledges 44 of spinal rod supports 26.

In some embodiments, as shown in FIGS. 17-19, one or more of the components of spinal implant system 10 can be easily revised if a revision surgery were to occur. In some embodiments, set screw 22 can be removed from body 14. Once set screw 22 is removed, spinal rod support 26 can be removed from body 14, as shown in FIGS. 17 and 18. Once spinal rod support 26 is removed, a tool can be placed thru crown 24 to engage portion 78 of shaft 18.

Figure 15:
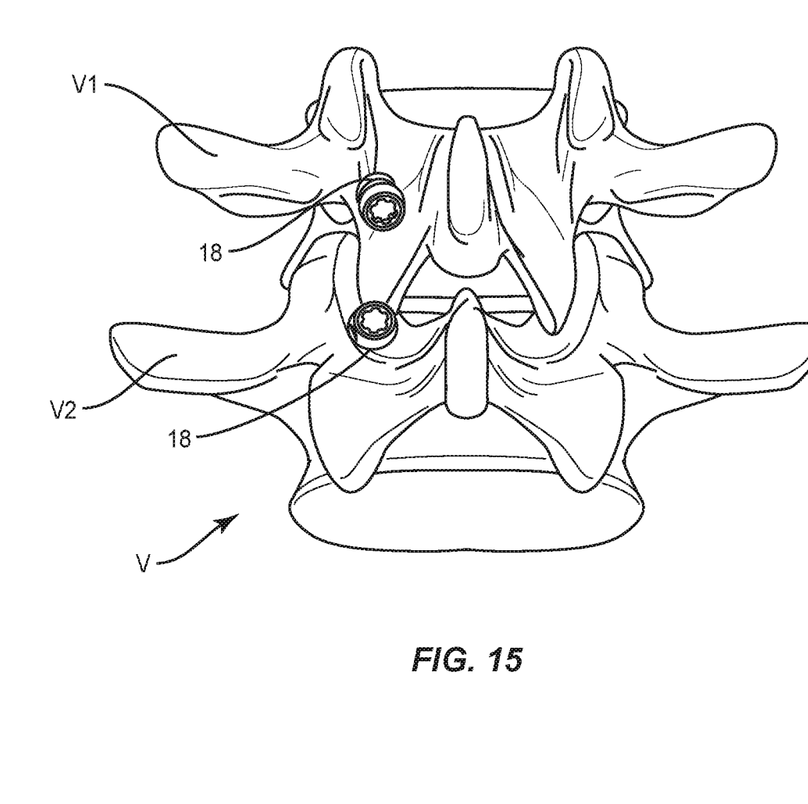
FIG. 15 is a plan view of components of one embodiment of a system in accordance with the principles of the present disclosure disposed with vertebrae.
Figure 16:
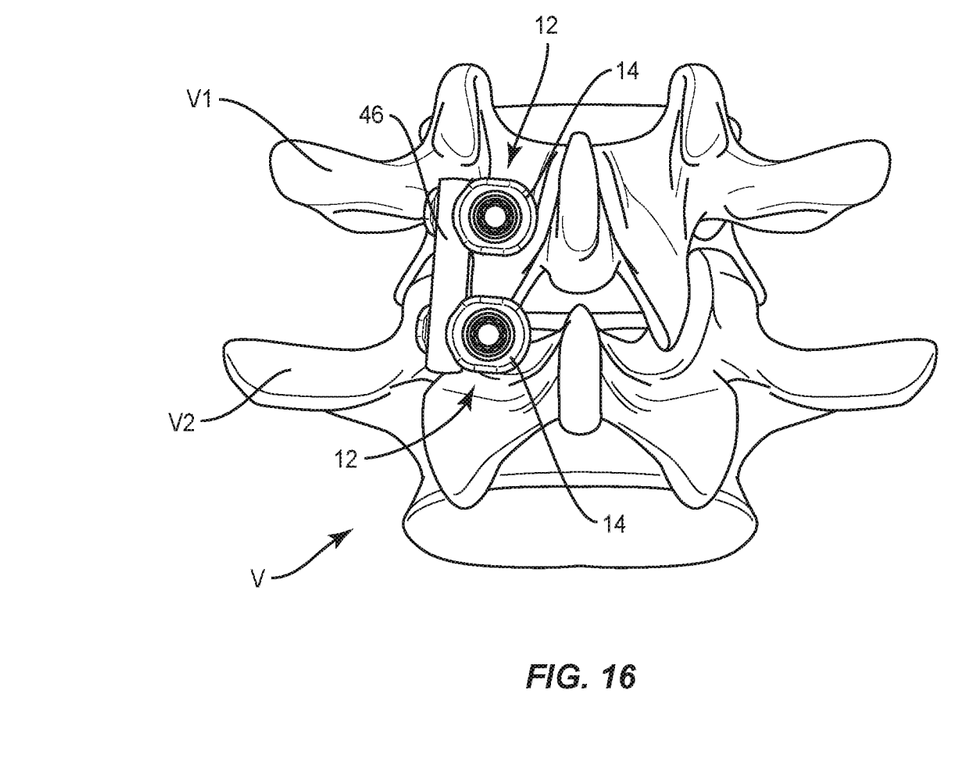
FIG. 16 is a plan view of components of one embodiment of a system in accordance with the principles of the present disclosure disposed with vertebrae.

In use, for treatment of a spinal disorder, one or more bone fasteners 12 including shaft 18 and body 14 can be threaded and engaged with tissue. In some embodiments, bone fastener 12 is disposed adjacent vertebrae V at a surgical site and is manipulated to drive, torque, insert or otherwise connect shaft 18 with vertebrae V1 and V2 in connection with a surgical procedure, as described herein. In some embodiments, body 14 is connected to shaft 18 and spinal rod 46 in a single vertebral level construct configuration that allows for compression, as shown in FIGS. 15 and 16.

One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member defining a plurality of grooves and including a removable support;
   a coupling member disposed with the first member;
   a first band configured for disposal within the grooves;
   a second band configured for disposal within the grooves;
   a second member configured to penetrate tissue and including a head engageable with the first band to provisionally connect the first member to the second member; and
   a part releasably engaged with the first member,
   the coupling member being engageable with the removable support, and the coupling member being engageable with the part to move the part relative to the first member into engagement with the second band to dispose the second band adjacent the first band to connect the first member to the second member.

2. A bone fastener as recited in claim 1, wherein the part releasably engages with the first member by a releasable friction fit.

3. A bone fastener as recited in claim 2, wherein the coupling member applies a force to the part to overcome the friction fit and axially translate the part relative to the first member.

4. A bone fastener as recited in claim 3, wherein the coupling member applies a force in a range of 80-350 N to the part to overcome the friction fit.

5. A bone fastener as recited in claim 1, wherein the part releasably engages with the first member by a releasable snap fit.

6. A bone fastener as recited in claim 1, wherein the part includes a projection engaged in a friction fit with the first member.

7. A bone fastener as recited in claim 6, wherein the projection includes a circumferential flange.

8. A bone fastener as recited in claim 6, wherein the first member includes a projection engaged in a friction fit with the projection of the part.

9. A bone fastener as recited in claim 1, wherein the coupling member includes a set screw having a break off portion.

10. A bone fastener as recited in claim 1, wherein the coupling member includes a distal surface engageable with a proximal surface of the part.

11. A bone fastener as recited in claim 1, wherein the coupling member is rotatably fixed in rotation relative to the part.

12. A bone fastener as recited in claim 1, wherein the first member and the second member are engageable in a snap-fit assembly.

13. A bone fastener as recited in claim 1, wherein the first band is expandable between a provisional capture orientation and an expanded orientation, and the second band is expandable between a contracted orientation and an interference orientation to connect the members.

14. A single level spinal construct comprising:
   a first bone fastener including
      a body defining a plurality of grooves and including a removable spinal rod support,
      a set screw disposed with the body,
      a first band configured for disposal within the grooves and a second band configured for disposal within the grooves,
      a shaft configured to penetrate tissue and including a head engageable with the first band to provisionally connect the body to the shaft, and
      a crown releasably engaged with the body such that the set screw is engageable with the crown to move the crown relative to the body into engagement with the second band to dispose the second band adjacent the first band to connect the body to the shaft;
   a second bone fastener including a removable spinal rod support; and
   a spinal rod.

15. A single level spinal construct as recited in claim 14, wherein the crown releasably engages with the body by a releasable friction fit.

16. A single level spinal construct as recited in claim 15, wherein the set screw applies a force to the crown to overcome the friction fit and axially translate the crown relative to the body.

17. A single level spinal construct as recited in claim 14, wherein the set screw engages the spinal rod support of the first bone fastener to fix the spinal rod relative to the body.

18. A single level spinal construct as recited in claim 14, wherein the second bone fastener includes
   a body defining a plurality of grooves and including a set screw, and a first band and a second band configured for disposal within the grooves of the second bone fastener,
   a shaft configured to penetrate tissue and including a head engageable with the first band of the second bone fastener to provisionally connect the body and the shaft of the second bone fastener, and
   a crown releasably engaged with the body of the second bone fastener.

19. A single level spinal construct as recited in claim 18, wherein the crown releasably engages with the body of the second bone fastener by a releasable friction fit, and the set screw of the second bone fastener applies a force to the crown of the second bone fastener to overcome the friction fit and axially translate the crown relative to the body of the second bone fastener.

20. A spinal implant system comprising:
   at least one bone fastener including
      a body defining a plurality of grooves and including a removable support,
      a set screw disposed with the body,
      a first band configured for disposal within the grooves and a second band configured for disposal within the grooves,
      a shaft configured to penetrate tissue and including a head engageable with the first band to provisionally connect the body to the shaft, and
      a crown releasably engaged with the body such that the set screw is engageable with the crown to move the crown relative to the body into engagement with the second band to dispose the second band adjacent the first band to connect the body to the shaft,
   wherein the body is selected from a plurality of alternate bodies and the shaft includes a mating surface engageable with the body such that the shaft is interchangeable with the plurality of bodies.

* * * * *